United States Patent
Pinnell

(10) Patent No.: US 7,160,560 B2
(45) Date of Patent: Jan. 9, 2007

(54) SKIN-CARE COMPOSITION

(75) Inventor: Sheldon R. Pinnell, Durham, NC (US)

(73) Assignee: L'Oreal S.A., Paris (FR)

( * ) Notice: Subject to any disclaimer, the term of this patent is extended or adjusted under 35 U.S.C. 154(b) by 31 days.

(21) Appl. No.: 10/691,840

(22) Filed: Oct. 23, 2003

(65) Prior Publication Data

US 2005/0089500 A1  Apr. 28, 2005

(51) Int. Cl.
*A61K 36/00* (2006.01)
*A61K 31/133* (2006.01)

(52) U.S. Cl. .................................. 424/725
(58) Field of Classification Search .............. 424/725
See application file for complete search history.

(56) References Cited

U.S. PATENT DOCUMENTS

| | | | |
|---|---|---|---|
| 6,203,805 B1 * | 3/2001 | Collins et al. | 424/401 |
| 6,403,112 B1 | 6/2002 | Motitschke et al. | |
| 6,572,868 B1 * | 6/2003 | Cope | 424/400 |
| 2003/0157040 A1 | 8/2003 | Bunger et al. | |

OTHER PUBLICATIONS

Pirisi, A. Gently Does It Please!; The Gazette, Montreal, Que., Feb. 3, 1998, p. D1, pp. 1-3 of Proquest direct.*
Basset, A new treatment in Dermatology: Madecassol Tulgras, 1978, Vie Med. 59:9, 1708-1709.
Bonte, Influence of Asiatic Acid Madecassic Acid, and Asiaticoside on Human Collagen I Synthesis, 1993, Planta Med. 60: 133-135.
Bunger, RonaCare(TM) Ectoin-the innovative solution for skin care and angi-ageing concepts, 2003, http://www.ctmw.com/article2002.htm.
De Paepe, The role of ceramides in the barrier function of the skin and possible dermato-cosmetic applications, 1995, unknown.
De Paepe, Repair of acetone and sodium lauryl sulphate-damaged human skin barrier function . . . , 2002, JEADV 16: 587-594.
Laugier, Action of a titrated extract of Centella asiatica on cheloid scars, wound healing . . . , 1974, Medecine et Hygiene 1093: 455-456.
Maquart, Triterpenes from Centella asiatica stimulate extracellular matrix accumulation in rat experimental wounds, 1999, E. J. Derm. 9: 289-296.
Maquart, Stimulation of collagen synthesis in fibroblast cultures by a triterpine extracted from Centella asiatica, 1990, Conn. Tiss. Res. 24: 107-120.
Monteil, Titrated extract of Centella asiatica in cicatrization of burns, 1969, Feuillets du practicien 34, 8.
Punto, Skin lipids, the lipid barrier and barrier repairing ingredients, 2003, Tech Notes, Aug. 18, 2003.
Tenni, Effect of the triterpenoid fraction of Centella asiatica on macromolecules . . . , 1987, unknown publication site.
Viala, Study of the transcutaneous permeationof the active ingredients of titrated extract of Centella asiatica . . . , 1977, Therapie 32:573.
Product literature-RonaCare(TM) Ectoin, unknown date, Merck KGaA, Darmstadt, Germany.
Product literature-Bois II, unknown date, Barnet Products Corp., Englewood Cliffs, NJ.
Product literature-BMX(TM) Complex, unknown date, Barnet Products Corp., Englewood Cliffs, NJ.
Product literature-SK-influx, unknown date, Centerchem, Inc., Stamford, CT.

* cited by examiner

*Primary Examiner*—Patricia Leith
(74) *Attorney, Agent, or Firm*—Lynn E. Barber

(57) ABSTRACT

A skin-care composition containing a protective component providing protection of the skin from environmental damage and regulating natural moisture of the skin; a skin firming component; and a barrier component. Thus, the composition includes at least one component that supports the collagen structure, and at least one component that supports the body's own defense/repair mechanisms, and most preferably, at least one component that supports the skin lipid system.

18 Claims, No Drawings

SKIN-CARE COMPOSITION

BACKGROUND OF THE INVENTION

1. Field of the Invention

This invention relates to skin-care compositions, and in particular, pertains to a skin-firming cream and an eye-firming cream, comprising at least one component that supports the collagen structure (firming), and at least one component that supports the body's own defense/repair mechanisms (protective), and most preferably, at least one component that supports the skin lipid system (barrier).

2. Description of the Related Art

Under normal conditions, human skin is capable of regulating its own moisture content, until the normal aging process sets in and skin generally becomes dryer. There are numerous prematurely occurring skin problems, however, such as dry skin, sagging skin, and other prematurely aging skin conditions and skin damage, that may occur in individuals of any age if they are exposed to harsh environmental conditions, such as over-exposure to the sun's rays. Thus, active young adults in their mid to upper 20's to their 40's may find to their dismay that their skin is beginning to have problems that are normally associated with much older people, particularly if they spend much time outside with their skin exposed without protection to sunlight, wind, and/or low humidity.

Because the treatment of skin problems is complex, and because most of these prior products are aimed at a particular limited aspect of skin damage, multiple products must be used to address the problems. A large portion of the cosmetic industry is devoted to trying to remedy one or more these skin problems, such as by providing various creams, lotions and other products. These skin-care products range from simple moisturizing preparations, containing main ingredients such as glycerin or tocopheryl acetate, to complicated formulations designed to prevent or repair particular types of skin damage. The moisturizing preparations generally rely either on occlusive substances that form a barrier on the skin, for example, paraffin or petrolatum, so that water is prevented from transdermally escaping through the skin, or on intradermal substances, such as glycerol that bind the water in the skin.

There are many skin-care products that include plant extracts. Examples include the composition of Pinnell (U.S. Pat. No. 6,524,599) containing milk thistle extract, soybean protein and alpha tocopherol, either singly or in combination. The disclosure of this patent and all other patents and publications referred to herein is incorporated herein by reference.

An example of a natural non-botanic product found to improve and stabilize the hydration of the human skin is ectoin, (s)-1,4,5,6-tetrahydro-2-methyl-4-pyrimidinecarboxylic acid ($C_6H_{10}N_2O_2$) obtained from extremely halophilic bacteria, such as *Ectothiorhodospira halochloris*, found in salt lakes, saline soils, deserts and seawater. Ectoin is known to play a role in the osmoregulation of these organisms, being compatible with the metabolism of the cells, even in high concentrations. Ectoin is amphoteric and binds water molecules, forms large hydration shells, stabilizes the natural structure of biopolymers such as proteins, nucleic acids and biomembranes, and minimizes the denaturation of these biopolymers that usually occurs when water is lost, by counteracting this process. See U.S. Pat. No. 6,403,112. As a cosmetic raw material, ectoin has been found to protect the skin from being damaged by environmental stress factors, such as heat, cold, UV radiation, and harmful environmental chemicals, by supporting the repair and protective mechanisms of the cells. For example, studies have shown that ectoin inhibits the signaling cascade brought about by UVA-radiation in human keratinocytes as well as UVA radiation-induced formation of mitochondrial DNA mutations in human dermal fibroblasts. In addition, ectoin regulates the natural moisture in cells, preventing them from drying out, so that the skin remains moist and supple for a longer period of time, protects cell membranes against various surfactants, helps to inhibit the formation of sunburn cells, induces faster formation of heat-shock proteins, and protects the skin immune system by preventing damage to Langerhans cells. Commercially produced ectoin (RONACARE™, Ronacare, division of Merck KGaA, Darmstadt, Germany) contains about 96% ectoin, with the remainder being hydroxyectoin and trace elements. It is easily accepted by the cells, is compatible with the cells' inherent metabolism, has a high level of activity, is non-toxic and chemically and biologically stable.

*Centella asiatica*, or tiger grass, is a perennial creeping tropical plant, that has been known and used by East Indian, American Indian, Chinese and Indonesian traditional doctors for thousands of years for wound-healing, sedative, analgesic and antibiotic treatments. For about 30 years, pharmaceutical products have been taking advantage of the healing properties of *Centella asiatica*, successfully using it to accelerate post procedure healing, to stop the inflammatory phase of hypertrophic scars and keloids and many other indications. The active constituents of *C. asiatica* are two triterpenic saponines, asiaticoside and madecasoside, which are derived respectively from asiatic acid (2 Ó, 6β, 24-trihydroxy-urs-12 (13)-en-28 oic) and madecassic acid (2 Ó, 6β, 24 Ó-tetrahydroxy-urs-12 (13)-en-28 oic). These constituents are not very abundant when using a standard plant extract of *Centella asiatica*. The titrated extract of the leaves of *Centella asiatica* (TECA), used herein, is a standardized product of Roche Nicholas Laboratories. TECA is the combination of three of these active ingredients—asiatic and madecassic acid (54–66%) and asiaticoside (36–44%). It is used for wound-healing, for example, by increasing the cellular proliferation and collagen synthesis at the wound site, venous insufficiency, anti-wrinkle toning, cellulite and stretch marks, and has also been found to be effective in the cicatrisation of burns, as well as providing healing and soothing properties to the skin. Extracts of *Centella asiatica* containing various levels of the active ingredients have also been shown to have effectiveness in wound healing and related treatments, as well as to have anti-microbial properties.

To prevent harmful substances from adhering to or entering the skin, and to prevent transepidermal water loss, various skin barrier products have been produced that provide an intact coating over the skin. Petrolatum products, such as AQUAPHOR™, provide a simple barrier, but do not help in skin repair. Other products have also been formulated for skin barrier repair. In human skin, ceramides are the major lipid constituents of the stratum corneum and play a crucial role in the skin barrier function and water retention in the skin. A balance of cholesterol, ceramides, glycosylated ceramides and triglycerides (barrier and physiologic lipids) is essential to maintain optical skin condition. Glycosphingolipids, such as ceramides, which promote differentiation, and glycosylated ceramides, which enhance proliferation, have been shown to play a role in maintaining an intact skin surface barrier. The BMX™ complex of Barnet Products Corp. (Englewood Cliffs, N.J.) is a lipid complex that mimics biological membranes and provides a stable matrix, and creates a delivery system to suspend the critical components and facilitate delivery into the stratum corneum of the skin. BMX™ complex comprises lipids isolated from plant material (*Hordeum vulgare* (barley) and *Solanum lycopersicum* (tomato)) and helps in lipid retention in the skin. In particular, the various plant extracts in this product are combined in a final ratio to yield a composition approximately as follows: 20% phytosterols, 30% triglycerides, 40% hydrocarbons and branched esters, 10% ceramides and other phytosphingolipids.

SEPILIFT DPHP™ (dipalmitoyl hydroxyproline)(Seppic, Fairfield, N.J.) exhibits triple firming action: it stimulates remodeling and contraction of collagen fibers, protects elastic fibers against enzymatic breakdown, and scavenges free radicals. Products containing SEPILIFT DPHP™ include moisturizers and lip conditioners.

BOIS II™ (Barnet Products Corp., Englewood Cliffs, N.J.) is a proprietary raw material containing various polar and non-polar lipids from *Santalum album* (sandalwood), *Phellodendron amurense* bark (cork tree), and *Hordeum distichon* (barley grain) extracts. The extract is obtained from aged wood pulp and grains, which are washed and dried, then ground to a fine powder and extracted with grain oil as an extraction medium, without the use of solvents, to yield medium chain hydrocarbons, long chain alcohols, glycolipids, flavonoids, fatty acids and triglycerides. It specifically contains various lipids inherent to these plants extracted in a proprietary process that yields, among others, medium chain hydrocarbons, glycolipids, fatty acids and triglycerides, all of which are essential constituents of the lipid barrier of the skin. BOIS II™ has been found to reduce transepidermal water loss, increase skin hydration, and improve skin suppleness.

The skin around the eyes is particularly susceptible to damage from environmental stressors or stressful lifestyles, such as sagging, undesirable dark circles, or puffiness. Thus, for treatment of the skin beneath the eyes, cosmetic ingredients that are aimed at addressing one or more of these conditions have been produced. One such product is EYE-LISS™ (Sederma S. A., member of Croda International Group, Le Perray-En-Yvelines, France), which contains three active substances: hesperidin methyl chalcone (5%), derived from a flavonoid, hesperidin, present in citrus fruits, which decreases capillary vessel permeability; dipeptide valyltryptophan (VW)(0.1%), a peptide from the traditional Japanese fermented rice beverage sake, which increases the frequency of lymphangion contraction; and palmityoyl-Gly-Gln-Pro-Arg (Pal-GQPR)(300 ppm) SEQ ID NO: 1, a fragment of human immunoglobulin, which restores skin elasticity and firmness, plus water, glycerin, and steareth 20 dipeptide-2 ("dipeptide"). This combination addresses the problems of capillary permeability related to irritation, hypertension, tiredness and the effects of age causing the walls of the network of vessels crossing the eyelid to have increased leakage of water and protein into surrounding tissues, especially sub-orbitally. It also reduces the tissue sagging and inflammation that contribute to fluid stasis, and reduces the problem of insufficient lymphatic drainage. This is because hesperidin methyl chalcone, derived from Hesperidin, has anti-edematous properties and decreases capillary permeability, dipeptide increases the frequency of lymphangion contraction, thereby enhancing the removal of fluids, and Pal-GQPR, a fragment of human immunoglobin, acts on secretion of cytokine IL6, thereby helping preclude inflammations.

An additional preferred component of the eye-firming cream is SK-INFLUX™ (Centerchem, Inc., Stamford, Conn.), which helps to maximize the skin barrier, and essential factor in the delicate eye area where the skin thickness is only that of approximately 3–5 sheets of paper. SK-INFLUX™ is a lipid concentrate used to improve the skin barrier, through moisturization, anti-aging and anti-wrinkle effects, skin repair, and skin protection. The lipid concentrate includes a ceramide complex (1.5%), which contains ceramide I (0.001%), ceramide III (0.5%), ceramide IIIB (0.5%), and ceramide VI (0.5%); cholesterol. (1.5%), free fatty acid (about 3.5%) and phytosphingosine (0.5%). Ceramides I, III and VI are required in restoration of damaged and sensitive skin.

It is therefore an object of the invention to provide a single skin-firming cream that enhances collagen biosynthesis, improves cell repair, supports the skin immune system, and improves the skin barrier. It is a further advantage to provide an eye-firming cream with these same features, plus having the benefit of repairing bags under the eyes as well as working to prevent their formation.

Other objects and advantages will be more fully apparent from the following disclosure and appended claims.

SUMMARY OF THE INVENTION

The invention herein is a skin-care composition comprising a protective component providing protection of the skin from environmental damage and regulating natural moisture of the skin; a skin firming component; and a barrier component. In particular, the invention herein comprises at least one component that supports the collagen structure, at least one component that supports the body's own defense/repair mechanisms, and at least one component that supports the skin lipid system.

Other objects and features of the inventions will be more fully apparent from the following disclosure and appended claims.

DETAILED DESCRIPTION OF THE INVENTION AND PREFERRED EMBODIMENTS THEREOF

The present invention provides unique compositions for topical application to the skin. In particular, the preferred embodiments of the invention herein include a skin-firming cream and an eye-firming cream. The skin-firming cream is aimed at being the first line of defense against environmentally-induced skin damage and the age-related slowing of biological repair mechanisms. Utilizing the results of clinical science and biotechnological research, this product is designed to enhance the synthesis of collagen for firmer skin while giving repair and immune mechanisms in the cells a boost to accelerate repair of damages from such aggressors as ultraviolet radiation, pollutants and chemicals, and to help preclude further damage.

In the preferred embodiments, both the skin-firming cream and the eye-firming cream of the invention comprise at least one first component that supports the collagen structure and at least one second component that supports the body's own defense/repair mechanisms. The most preferred embodiments of the invention also comprise at least one third component that supports the skin lipid system (the skin lipids). The selection of the particular component(s), such as the particular component that supports the skin lipid system, is primarily based on component effectiveness and compatibility with the rest of the formulation.

Preferably, in all of the skin and eye firming creams of the invention, the at least one first component that supports the collagen structure comprises ectoin and the at least one second component that supports the body's own defense/repair mechanisms comprises an extract of *Centella asiatica*. In the preferred embodiments, the firming creams of the invention comprise about 4% ectoin, and 0.5% *Centella Asiatica* extract, and most preferably 0.2–4% ectoin and 0.2–1% *Centella Asiatica* extract.

The preferred third component that supports the skin lipid system is BMX™, preferably, 0.5–2% BMX™. Additional lipids may also be added as are known in the art, examples of which are presented herein. Thus, the preferred skin-firming cream formulation includes: BMX™ Complex, SEPILIFT DPHP™, and BOIS II™. The combination of the preferred ingredients provides a single skin-firming cream product that enhances collagen biosynthesis, improves cell repair, supports the skin immune system and improves the skin barrier.

Optionally, the composition of the invention may also comprise additional ingredients that are known to support one or more of these three key areas. (for example, BOIS™ for face products and SK-INFLUX™ for the eye creams with regards to skin barrier, and SEPILIFT™ for the face product with regards to collagen support), a skin-firming agent, as well as other optional components.

The eye-firming cream of the invention offers the same benefits as the skin-firming cream, plus additionally addressing the symptoms specific to the delicate eye area, such as dark circles and puffiness, often brought on by environmental stressors or frenetic lifestyles. The main ingredients of the preferred eye-firming cream are again the *Centella asiatica* extract, ectoin, and EYELISS™, a product containing a combination of hesperidin methyl chalcone, dipeptide and Pal-GQPR. In addition, the preferred eye-firming creams comprise SK-INFLUX™, containing a ceramide complex.

The compositions of the invention herein can comprise, consist essentially of, or consist of, the ingredients and components described herein. As used herein, the term "consisting essentially of" means that the composition or component may include additional ingredients, but only if the additional ingredients do not materially alter the basic and novel characteristics of the claimed compositions or methods.

The features of the present invention will be more clearly understood by reference to the following examples, which are not to be construed as limiting the invention. In the formulation examples herein, components not discussed specifically above are standard cosmetic ingredients, used for example as moisturizers, stabilizers, preservatives, scents and the like by those of ordinary skill in the art.

EXAMPLE 1

Preparation of Skin-Firming Cream

This formulation includes Phases A–G, and is prepared as follows. The preferred ingredients are shown in Table 1.

TABLE 1

| Phase | Name | Percent |
|---|---|---|
| A | Deionized Water | 72.14 |
|   | Disodium EDTA | 0.10 |
|   | Ectoin | 2.00 |
| B | Ammonium acryloyldimethyltaurate/VP copolymer | 0.90 |
| C | Dipalmitoyl hydroxyproline | 1.00 |
|   | Bois II ™ | 6.00 |

TABLE 1-continued

| Phase | Name | Percent |
|---|---|---|
|   | Cetyl alcohol | 1.10 |
|   | C12–15 alkyl benzoate | 5.00 |
|   | Caprylic/capric triclyceride | 3.00 |
|   | BMX ™ complex | 1.00 |
|   | Tocopheryl acetate | 1.00 |
| D | Polyacrylamide, C13–14 isoparaffin, LAURETH-7 ™ | 1.00 |
| E | TECA EXTRACT ™ | 0.50 |
|   | Ethoxydiglycol | 4.00 |
|   | Phenoxyethanol, methyl, butyl, ethyl & propylparaben | 1.00 |
| F | Triethanolamine | 0.20 |
| G | Juniper oil | 0.06 |

The percentages given for the components of each phase are percent by weight of the entire finished formulation, not of the individual phase. Phase A, containing 72.14% water; 0.10% disodium EDTA (ethylene diamine tetraacetic acid); and 2.00% ectoin (RONA-CARE™, Merck KGAA, Darmstadt, Germany), is mixed in a main vessel and heated to 65–70° C.

While Phase A is heating, Phase B, which is 0.90% ARISTOFLEX AVC™ (ammonium acryloyldimethyltaurate/VP copolymer, made by Clariant (Germany), is sprinkled into Phase A, and the mixture is mixed until no lumps are present.

In a separate vessel, Phase C, containing 1.00% SEPILIFT DPHP™ (dipalmitoyl hydroxyproline)(Seppic, Fairfield, N.J.); 6.00% BOIS II™ (*Santalum album* wood extract, *Phellodendron amurense* bark extract, and *Hordeum distichon* extract)(Barnet Products Corp., Englewood Cliffs, N.J.); 1.10% LIPOCOL C™ (cetyl alcohol)(Lipo Chemicals); 5.00% FINSOLV TN™ (C-12–15 alkyl benzoate) (Finetex, Elmwood Park, N.J.); 3.00% TEGOSOFT CT™ (caprylic/capric triglyceride)(Goldschmidt-Degussa, Essen, Germany); 1.00% BMX™ complex (*Hordeum vulgare* extract, *Solanum lycopersicum* extract)(Barnet); and 1.00% Vitamin E acetate (tocopheryl acetate)(Roche Vitamins, Inc., Parsippany, N.J.), is mixed and heated to 65–70° C.

Phase C is slowly added into Phase A and the combination is mixed until uniform. Sweepers are then used as is known in the art to homogenize the combined Phases A–C for 5 minutes.

Phase D, comprising 1% SEPIGEL 305™ (polyacrylamide and C 13–14 isoparaffin and LAURETH 7™)(Seppic, Fairfield, N.J.), is added to Phases A–C and the result further homogenized for 5 minutes. Mixing is switched to propeller mixing as is known in the art and the combined Phases A–D are cooled to 45° C.

Phase E, comprising 0.5% TECA EXTRACT™ (*Centella asiatica* extract)(Roche Nicholas Laboratories, France); 4.00% TRIVALIN SF™ (ethoxydiglycol)(Trivent Chemical Company, Inc., Monmouth Junction, N.J.); and 1.00% PHENONIP™ (phenoxyethanol, methylparaben, butylparaben, ethylparaben and propylparaben)(Clariant, Germany), is premixed and warmed until a clear solution is obtained, and is then added to the combined Phases A–D, and the final mixture is mixed until uniform.

Phase F, comprising 0.20% TEA 99% (triethanolamine) (generic) is added to the combined Phases A–E and the combination mixed until uniform.

Phase G, comprising 0.06% juniper oil 292750 (Premier Specialties, Middlesex, N.J.) is added to the combined Phases A–F and the combination mixed until uniform.

The final mixture is then cooled to room temperature (20–25° C.).

The overnight viscosity of the final mixture is 80,000 cP (Brookfield DV-I+ Digital Viscometer (T-C @5 RPM). The pH is 4.82.

EXAMPLE 2

Preparation of Eye Firming Cream

This formulation includes Phases A–G, and is prepared as follows. The preferred ingredients are shown in Table 2.

TABLE 2

| Phase | Name | Percent |
|---|---|---|
| A | Deionized Water | 69.44 |
|   | Disodium EDTA | 0.10 |
|   | Ectoin | 2.00 |
| B | Hyaluronic acid sodium salt | 0.10 |
| C | Cetearyl glucoside | 1.00 |
| D | Cetyl alcohol | 2.00 |
|   | Glyceryl stearate, PEG-100 stearate | 1.50 |
|   | Cyclopentasiloxane | 5.00 |
|   | Cyclopentasiloxane, dimethicone\vinyl dimethicone crosspolymer | 5.00 |
|   | SK-INFLUX ™ | 0.50 |
|   | Dimethicone | 0.50 |
|   | Polyurethane/silica | 2.00 |
|   | Tocopherol acetate | 1.00 |
| E | Polyacrylamide, C13–14 isoparaffin, LAURETH-7 ™ | 1.50 |
| F | EYELISS ™ | 3.00 |
| G | TECA EXTRACT ™ | 0.30 |
|   | Ethoxydiglycol | 4.00 |
|   | Phenoxyethanol, methyl, butyl, ethyl & propylparaben | 1.00 |
| H | Juniper oil | 0.06 |

The percentages given for the components of each phase are percent by weight of the entire finished formulation, not of the individual phase.

Phase A, containing 69.44% water; 0.10% disodium EDTA (ethylene diamine tetraacetic acid); and 2.00% ectoin (RONACARE™, Merck KGaA, Darmstadt, Germany), is mixed in a main vessel and heated to 65–70° C.

Phase B, 0.10% sodium hyaluronate (Actives International, Ramsey, N.J.) is slowly sprinkled into Phase A, and mixing is continued until all of Phase B is dissolved.

Phase C, comprising 1% TEGO CARE CG 90™ (cetearyl glucoside)(Goldschmidt-Degussa) is sprinkled into the combined Phases A–B and mixed and heated to 65–70° C.

In a separate vessel, Phase D is mixed and heated to 65–70° C. Phase D contains 2.00% LIPOCOL C™ (cetyl alcohol)(Lipo Chemicals); 1.50% LIPOMULSE 165™ (glyceryl stearate and PEG-100 stearate)(Lipo Chemicals); 5.00% CYCLOMETHICONE™ (cyclopentasiloxane)(Silicones Plus, Inc., Arlington, Tex.); CSFE 938™ (94.5% cyclopentasiloxane and 5.5% dimethicone/vinyl dimethicone crosspolymer)(Silicones Plus, Inc., Arlington, Tex.); 0.50% SK-INFLUX™ (ceramide 3, ceramide 6-II, ceramide 1, phytosphingosine, cholesterol, sodium lauroyl lactylate, carbomer, xanthan gum, methylparaben, propylparaben and water)( Centerchem, Inc., Stamford, Conn.); 0.50% DIMETHICONE 200™ (dimethicone)(Dow Corning); 2.00% BPD-500™ (97% polyurethane and 3% silica)(Dow Corning); and 1.00% vitamin E acetate (tocopherol acetate) (Roche Vitamins Inc.).

Homogenization is begun of the combined Phases A–D, and Phase E is added. Phase E comprises 1.5% SEPIGEL 305™ (polyacrylamide and C 13–14 isoparaffin and LAURETH 7™)(Seppic). Homogenization is continued for 5 minutes, and then propeller mixing is begun and the mixture allowed to begin cooling.

When the temperature of the mixture reaches 45° C., Phase F, comprising 3.00% EYELISS™ (water, glycerin, hesperidin methyl chalcone, steareth 20 dipeptide-2, palmitoyl tetrapeptide-3)(Sederma) is added and mixed in until uniform.

Phase G is added and mixed in. Phase G comprises 0.30% TECA EXTRACT™ (*Centella asiatica* extract)(Roche Nicholas Laboratories); 4.00% TRIVALIN SF™ (ethoxydiglycol)(Trivent); and 1.00% PHENONIP™(phenoxyethanol, methylparaben, butylparaben, ethylparaben and propylparaben)(Clariant).

Phase H, comprising 0.06% juniper oil 292750 (Premier Specialties, Middlesex, N.J.) is added to the combined Phases A-G and the combination mixed until uniform.

The final mixture is then cooled to room temperature (20–25° C.). The pH of the final lotion is 5.41.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A composition for application on skin, comprising:
 a) a first component supporting skin collagen structure comprising ectoin; and
 b) a second component that supports body defense and repair mechanisms comprising an extract of *Centella asiatica* comprising asiatic acid, madecassic acid, and asiaticoside.

2. The composition of claim 1, comprising about 2% ectoin and 0.3–0.5% *Centella asiatica* extract.

3. The composition according to claim 1, further comprising a third component that supports skin lipids.

4. The composition of claim 3, further comprising a firming agent.

5. The composition of claim 4, wherein the firming agent is dipalmitoyl hydroxyproline.

6. The composition of claim 3, wherein the third component comprises a plant extract.

7. The composition of claim 6, wherein the plant extract comprises glycolipids, fatty acids and triglycerides extracted from sandalwood, cork tree bark, and barley grains.

8. The composition of claim 3, wherein the product is useful as an eye-firming cream, and the third component comprises a lipid complex.

9. The composition of claim 8, and wherein the lipid complex comprises a ceramide complex.

10. The composition of claim 9, wherein the ceramide complex comprises ceramide-3, ceremide 6-II, ceramide 1, phytosphingosine and cholesterol.

11. The composition of claim 9, wherein the composition comprises about 3% of the ceramide complex.

12. The composition of claim 8, further comprising hesperidin methyl chalcone, dipeptide, and peptide Pal-GQPR.

13. The composition according to claim 3, wherein the third component comprises a lipid complex.

14. The composition of claim 13, comprising about 2% ectoin and 0.3–0.5% *Centella asiatica* extract.

15. The composition of claim 14, comprising about 1% of the lipid complex.

16. The composition of claim 13, wherein the lipid complex is isolated from plants.

17. The composition of claim 16, wherein the lipid complex comprises phytosterols and triglycerides.

18. The composition of claim 17, wherein the lipid complex comprises 20% phytosterols, 30% triglycerides, 40% hydrocarbons and branched esters, 10% ceramides and other phytosphingolipids.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: attached to palmityoyl
<300> PUBLICATION INFORMATION:
<301> AUTHORS: Anon
<302> TITLE: Combating Bags under the Eyes
<303> JOURNAL: Product Literature, Sederma
<304> VOLUME: 1
<306> PAGES: 1-32
<307> DATE: 2002-04
<313> RELEVANT RESIDUES: (1)..(4)

```
-continued

<400> SEQUENCE: 1

Gly Gln Pro Arg
1
```